United States Patent
Jain et al.

(10) Patent No.: US 9,346,738 B2
(45) Date of Patent: May 24, 2016

(54) PROCESS FOR THE PREPARATION OF TREPROSTINIL AND DERIVATIVES THEREOF

(71) Applicant: SciPharm SàRL, Luxembourg (LU)

(72) Inventors: Nareshkumar Jain, Bristol, PA (US);
Michael Kirkup, Bristol, PA (US);
Michael Marella, Bristol, PA (US);
Sanjeevani Ghone, Bristol, PA (US)

(73) Assignee: SciPharm SaRL, Luxembourg (LU)

( * ) Notice: Subject to any disclaimer, the term of this patent is extended or adjusted under 35 U.S.C. 154(b) by 0 days.

(21) Appl. No.: 14/401,826

(22) PCT Filed: May 22, 2013

(86) PCT No.: PCT/EP2013/060472
§ 371 (c)(1),
(2) Date: Nov. 17, 2014

(87) PCT Pub. No.: WO2013/174848
PCT Pub. Date: Nov. 28, 2013

(65) Prior Publication Data
US 2015/0126761 A1 May 7, 2015

Related U.S. Application Data

(60) Provisional application No. 61/650,836, filed on May 23, 2012.

(30) Foreign Application Priority Data

Jun. 15, 2012 (EP) ..................................... 12172191

(51) Int. Cl.
| | | |
|---|---|---|
| C07C 59/115 | (2006.01) | |
| C07C 51/377 | (2006.01) | |
| C07C 47/565 | (2006.01) | |
| C07C 47/575 | (2006.01) | |
| C07F 7/18 | (2006.01) | |
| C07C 59/72 | (2006.01) | |
| C12P 31/00 | (2006.01) | |
| C12P 41/00 | (2006.01) | |

(52) U.S. Cl.
CPC ............. *C07C 51/377* (2013.01); *C07C 47/565* (2013.01); *C07C 47/575* (2013.01); *C07C 59/72* (2013.01); *C07F 7/18* (2013.01); *C07F 7/1844* (2013.01); *C07F 7/1852* (2013.01); *C07F 7/1892* (2013.01); *C12P 31/00* (2013.01); *C12P 41/002* (2013.01); *C12P 41/004* (2013.01); *C07C 2103/14* (2013.01)

(58) Field of Classification Search
USPC ................. 562/466, 468; 514/510, 13.7, 13.8
See application file for complete search history.

(56) References Cited

U.S. PATENT DOCUMENTS

| 6,242,842 B1 | 6/2001 | Pahl et al. |
|---|---|---|
| 6,700,025 B2 * | 3/2004 | Moriarty ................. C07C 39/17 544/154 |
| 2011/0118213 A1 | 5/2011 | Phares et al. |

FOREIGN PATENT DOCUMENTS

| WO | 2011/153363 A1 | 12/2011 |
|---|---|---|
| WO | 2012/009816 A1 | 1/2012 |

OTHER PUBLICATIONS

Bruce et al., "Claisen Rearrangement of meta-Substituted Allyl Phenyl Ethers", J. Chem. Soc., 1981, 2677-2679; 3 pgs.
El-Haggar et al., "Molecular design of small organic molecules based on a structural information for a conformationally constrained peptide that binds to G-CSF receptor", Bioorganic & Medicinal Chemistry Letters, 20(3), 1169-1172; 2010; 4 pgs.
El-Haggar et al., "Molecular design of small organic molecules based on a structural information for a conformationally constrained peptide that binds to G-CSF receptor" Supplementary Data, Bioorganic & Medicinal Chemistry Letters, 20(3), S1-S57; 2010; 57 pgs.
Kaiser et al., "Studies toward the Total Synthesis of Mumbaistatin, a Highly Potent Glucose-6-phosphate Translocase Inhibitor, Synthesis of a Mumbaistatin Analogue", Journal of Organic Chemistry, 67(26), 9248-9256; 2002; 9 pgs.
Moriarty et al., "The Intramolecular Asymmetric Pauson-Khand Cyclization as a Novel and General Stereoselective Route to Benzindene Prostacyclins: Synthesis of UT-15 (Treprostinil)", J Org Chem., 69(6):1890-902; 13 pgs.
International Search Report for International Patent Application No. PCT/EP13/60472 dated May 8, 2014; 22 pgs.
International Preliminary Report on Patentability for International Patent Application No. PCT/EP13/60472 dated Nov. 25, 2014; 15 pgs.
Partial European Search Report for European Patent Application No. 12172191.4 dated Oct. 17, 2012, 9 pgs.
Extended European Search Report for European Application No. 12172191.4 dated Feb. 25, 2013; 12 pages.

\* cited by examiner

*Primary Examiner* — Pancham Bakshi
(74) *Attorney, Agent, or Firm* — Loza & Loza, LLP; Michael Fedrick

(57) ABSTRACT

A method for the preparation of treprostinil and its derivatives is described. In contrast to prior art, this method utilizes an easily scalable enzymatic resolution of a key intermediate for making these compounds. Another significant improvement of the described method over prior methods is the regioselective Claisen rearrangement of a 5-allyloxy-benzaldehyde precursor, which is facilitated by a bromo substituent in 2-position.

17 Claims, No Drawings

PROCESS FOR THE PREPARATION OF TREPROSTINIL AND DERIVATIVES THEREOF

CROSS-REFERENCE TO RELATED APPLICATIONS

This application is the U.S. national stage of International Patent Application No. PCT/EP2013/060472, filed on May 22, 2013 and entitled IMPROVED PROCESS FOR THE PREPARATION OF TREPROSTINIL AND DERIVATIVES THEREOF, which claims the benefit of priority under 35 U.S.C. §120 from U.S. Patent Application No. 61/650,836, filed May 23, 2012 and under 35 U.S.C. §119 from European Patent Application No. 12172191.4, filed Jun. 15, 2012. The disclosures of the foregoing applications are incorporated herein by reference in their entirety.

FIELD OF THE INVENTION

The present invention relates to a shortened and more convenient process for producing treprostinil as well as novel intermediates useful in the process. Key features of the described process include a regioselective Claisen rearrangement of an allyloxy benzaldehyde precursor; tert-butyl-dimethylsilyl (TBDMS) protection of the alcohol moiety in the alkyne-bearing side chain during the non-stereoselective, intramolecular Pauson-Khand cyclization; and enzymatic kinetic resolution and subsequent chromatographic separation of two diastereomeric late-stage intermediates. The process of this application furnishes the benzindene prostacyclin treprostinil with more than 99% diastereomeric purity.

BACKGROUND OF THE INVENTION

Treprostinil is a synthetic analog of prostacyclin (PGI2), indicated for the treatment of pulmonary arterial hypertension (PAH). The major pharmacologic mechanisms of action of treprostinil are direct vasodilation of pulmonary and systemic arterial vascular beds and inhibition of platelet aggregation.

U.S. Pat. No. 6,700,025 discloses a process for the stereoselective synthesis of prostacyclin derivatives, in particular for treprostinil. However, this process and other known processes involve a large number of synthesis steps and chromatographic purifications. The objective of the present invention is the discovery of a process of increased utility that involves fewer steps and chromatographic purifications as well as a highly diastereoselective resolution of a key intermediate by enzymatic means that makes the process more suitable for scale-up.

SUMMARY OF THE INVENTION

The present invention relates to a process for preparing treprostinil and its derivatives and intermediates by a process that involves a kinetic enzymatic resolution step using a suitable lipase and a suitable acylating agent. The invention also relates to the novel synthesis of intermediates prepared during the synthesis of treprostinil (such as compounds of formula 4a, 5, 8, 9, 10, 11', 12', 13a, 14a, 15a, 16a, 16 and 17). Furthermore, the invention relates to the preparation of an allyl benzaldehyde intermediate via Claisen rearrangement of an allyloxy benzaldehyde precursor (compound of formula V) with increased regioselectivity due to the introduction of a halogen atom in the para position to the allyoxy group. Moreover, the invention relates to using a silyl protective group for the non-benzylic alcohol moiety of the C-11 side-chain.

DETAILED DESCRIPTION OF THE INVENTION

In one embodiment, the present invention relates to converting, via a Claisen rearrangement, a compound of the formula V

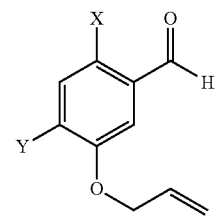

into a compound of the following formula VI

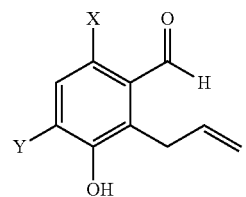

wherein X and Y are independently from one another either: Br, I, Cl, F, or H; preferably, X is Br and Y is H.

Due to the regioselective Claisen rearrangement no separation of regioisomers by chromatography or distillation is necessary. The required regioisomer can be obtained by recrystallization In another embodiment of the invention, a compound of the formula VII is obtained as an intermediate

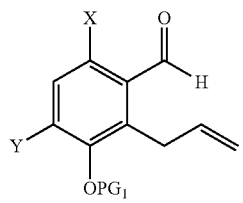

wherein X and Y are as defined above; and wherein $PG_1$ is a protective group for the phenol moiety such as methyl, methoxymethyl, benzyloxymethyl, methoxyethoxymethyl, benzyl, 4-methoxybenzyl, 2,6-dichlorobenzyl, 3,4-dichlorobenzyl; —CH$_2$C(O)—OR$_x$, or —CH$_2$CH$_2$OR$_x$. Preferably PG$_1$ is benzyl. R$_x$ is C$_{1-4}$ alkyl, or optionally substituted benzyl.

Alkyl refers to saturated straight-chain (unbranched) or branched hydrocarbon chains. Examples of representatives of individual groups are methyl; ethyl; n-propyl; isopropyl(1-methylethyl); n-butyl; 1-methylpropyl; isobutyl(2-methylpropyl); sec.-butyl(1-methylpropyl) and tert.-butyl(1,1-dimethylethyl);

In another embodiment of the current invention, an intermediate of the following structure VIII is obtained as the reactant in the non-stereoselective intramolecular Pauson-Khand cyclization

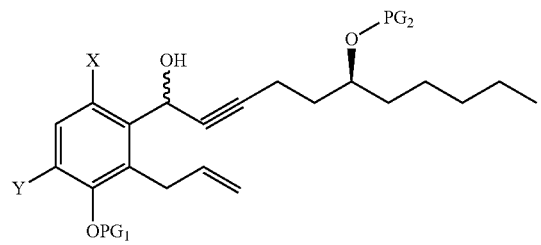

VIII wherein X, Y and PG$_1$ are as defined above; and wherein PG$_2$ is THP or a silyl alcohol protective group —SiR$_1$R$_2$R$_3$, wherein R$_1$, R$_2$, R$_3$ are independently from one another chosen from methyl, isopropyl, t-butyl, and phenyl, preferably R$_1$ and R$_2$ are methyl, and R$_3$ is t-butyl, or R$_1$, R$_2$ and R$_3$ are isopropyl, most preferably R$_1$ and R$_2$ are methyl, and R$_3$ is t-butyl.

Another embodiment of the current invention relates to the reduction with hydrogen gas and a suitable catalyst of a compound of formula IXa (mixture of two stereoisomers)

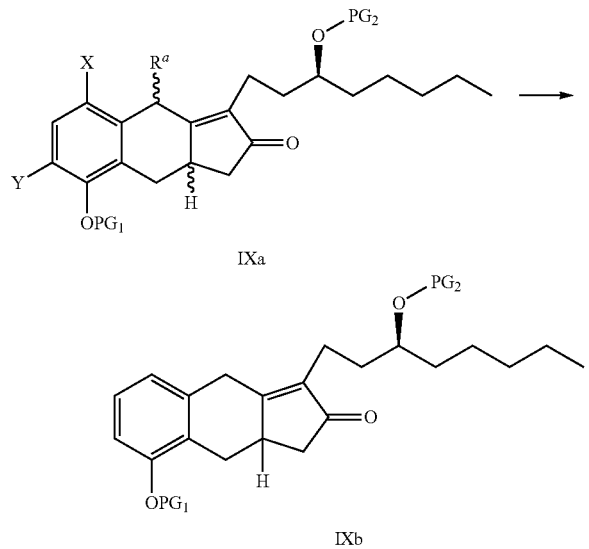

IXa

IXb to a compound mixture of the following formulas X and XI (mixture of two diastereomers)

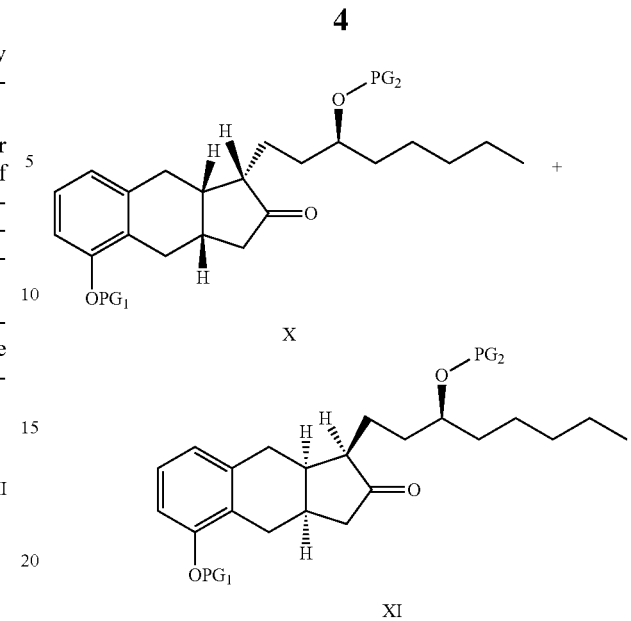

X

XI wherein X, Y, PG$_1$ and PG$_2$ are as defined above and wherein R$^a$ is H, OH, —OR$_x$, —O—PG$_1$, Br, I, Cl, F, —OAc, —OPiv, or —OCOR$_y$, —OCOOR$_y$, —SR$_y$ or —SO$_2$R$_y$, and wherein R$_y$ is C$_{1-4}$ alkyl or aryl.

Aryl denotes mono-, bi- or tricyclic carbon rings with at least one aromatic ring. Typical examples include phenyl, naphthyl, indanyl(2,3-dihydroindenyl), 1,2,3,4-tetra-hydronaphthyl and fluorenyl.

Another embodiment of the invention relates to the enzymatic resolution using a suitable lipase and a suitable acylating agent of a compound mixture of the following formulas XII and XIII

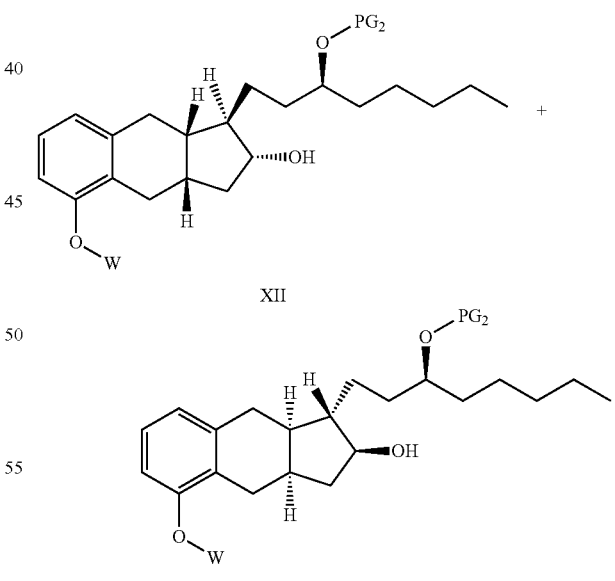

XII

XIII wherein PG$_2$ is defined as above; and W is selected from H, —CH$_2$CN, —CH$_2$COR$^4$, —CH$_2$CONR$^1$R$^2$, and —CH$_2$COSR$^3$; and wherein R$^1$ and R$^2$ are independently from one another selected from methyl, ethyl, i-propyl, n-butyl, morphinyl, piperidyl, and pyrrolidinyl; and R³ is methyl, ethyl, n-propyl, i-propyl, n-butyl, i-butyl, or phenyl; and R⁴ is —OCH₃, —OCH₂CH₃, —OCH₂CH₂CH₃, —OCH(CH₃)₂, —O(CH₂)₃CH₃, —OCH₂CH(CH₃)₂, or —OCH₂-Ph;

to compound mixture of the following formulas XIV and XV:

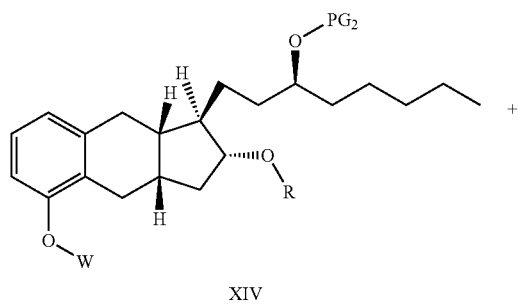

XIV

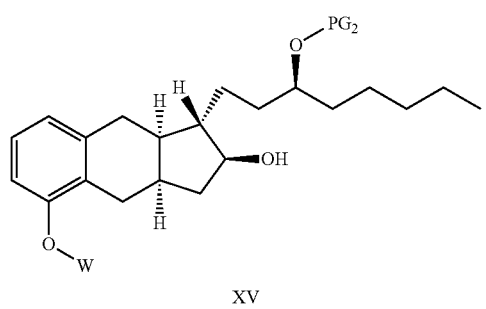

XV wherein PG₂ and W are as defined above and
R is an acyl group such as for example acetyl, ethanoyl, propanoyl, benzoyl or pivaloyl.

Preferably, PG₂ is TBDMS, R is acetyl, and W is —CH₂—CN, —CH₂COOH, or —CH₂COOR$_x$ and wherein R$_x$ is C$_{1-4}$ alkyl or benzyl.

Preferably, the above conversion is carried out by enzymatic acylation with a suitable lipase enzyme such as lipase from *Aspergillus niger* (Lipase AP6), lipase from *Candida rugosa* (CCL), lipase from porcine pancreas (PPL), lipase Amano AK, and lipase Amano PS30 in the presence of an appropriate acylating agent in an appropriate solvent such as C5 to C8 alkanes or alkanyl ethers.

Most preferably, the lipases used for the above conversion are lipase Amano AK and lipase Amano PS30. The preferred acylating reagent is vinyl acetate and the preferred solvents are hexane(s) or heptane(s).

Preferably, in the above conversion the acylated product is isolated from the non-acylated product by suitable means such as chromatography or crystallization, to give the acylated product in diastereomerically and enantiomerically pure form.

Diastereomerically pure means that the enzymatic acylation shown followed by separation of the acylated product from the non-acylated product produces the acylated diastereomer as represented by the above formula having a purity of >99%. The purity level is determined by running the product through an HPLC column packed with a stationary phase capable of separating enantiomers where >99% of the above diastereomer exits the column as a single enantiomerically and diastereomerically pure compound.

The present invention also relates to a method of making treprostinil utilizing the following reaction schemes (Schemes 1-3).

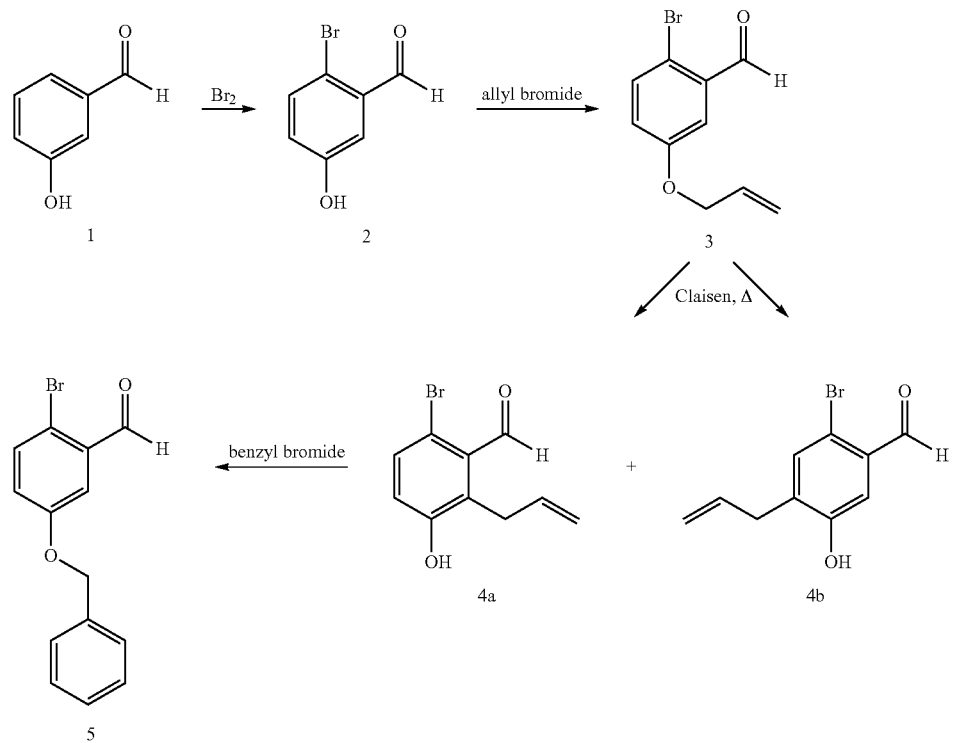

Scheme 1: Preparation of 2-allyl-3-benzyloxy-6-bromo-benzaldehyde (5).

Scheme 2: Preparation of (S)-tert-butyl-(1-but-3-ynyl-hexyloxy)-dimethyl-silane (10)
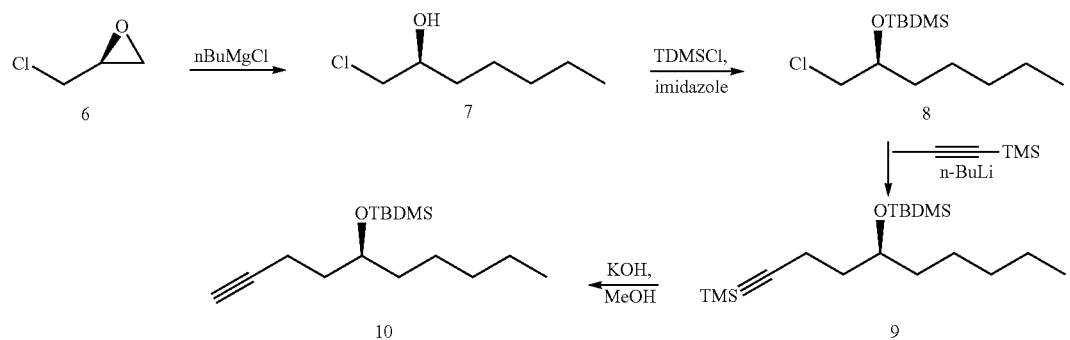

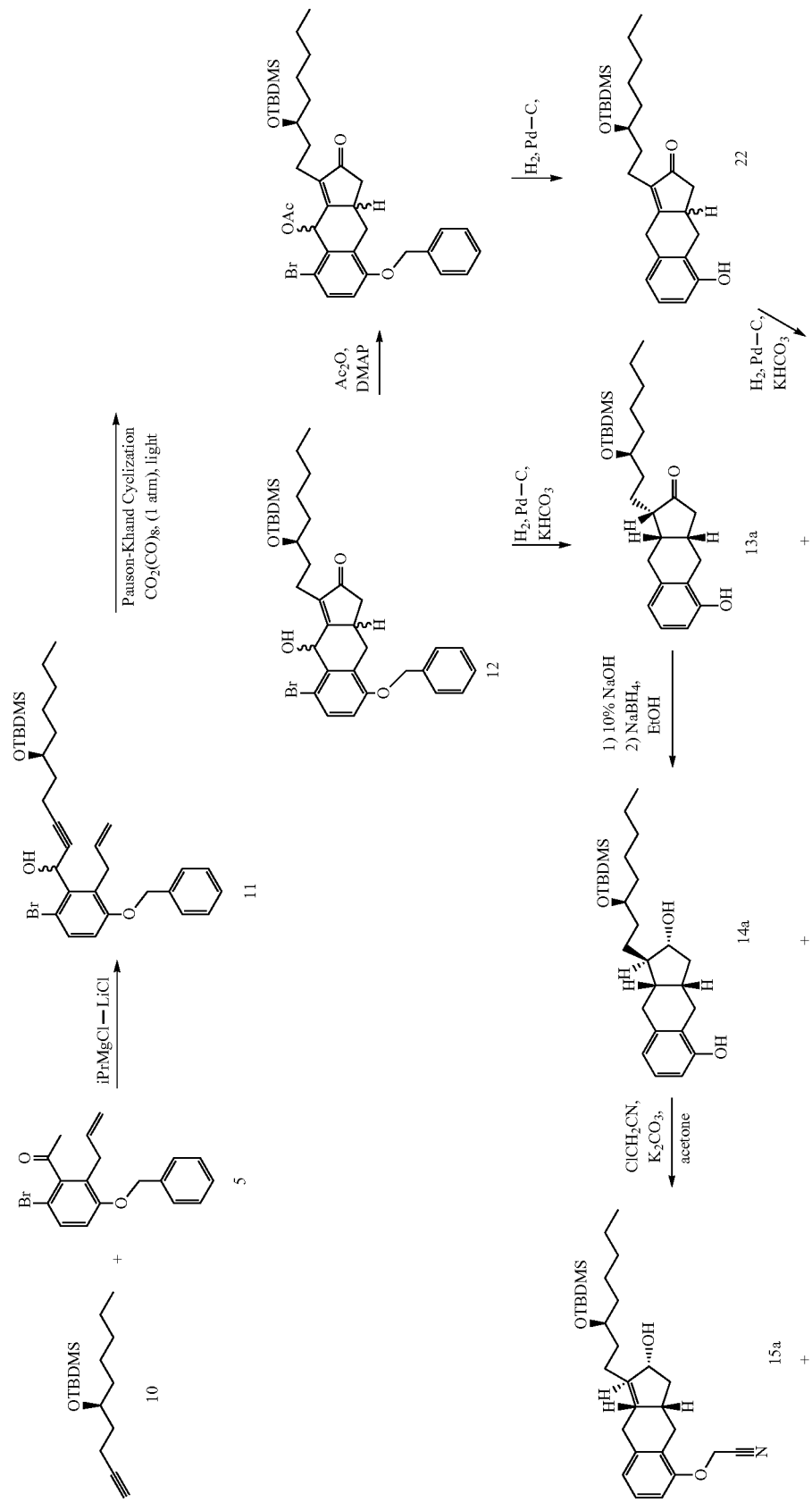

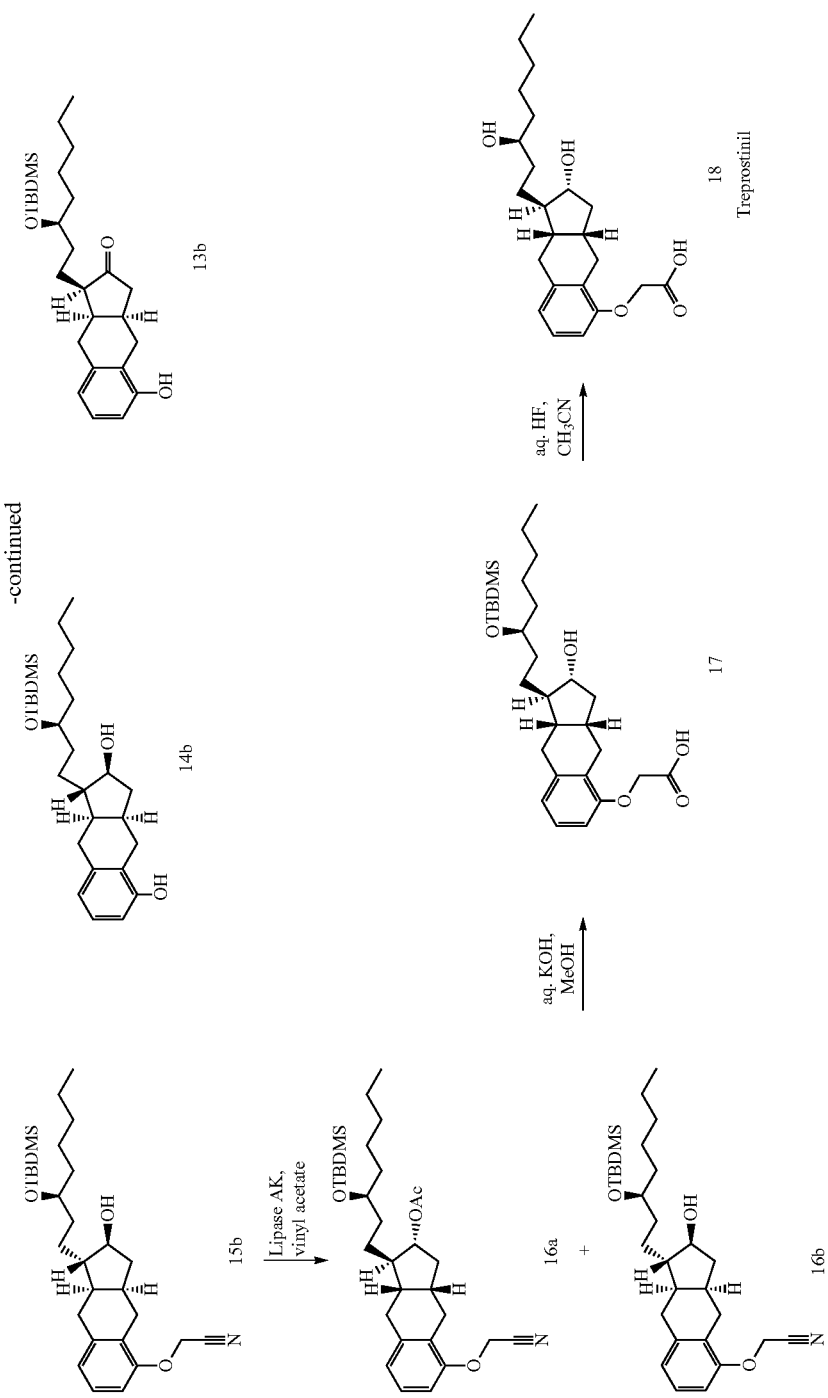

Another embodiment of the current invention relates to intermediate compounds of formula I, formula II, formula IIb, formula IIIb, or formula IVb

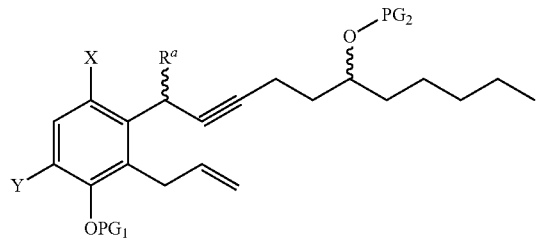
I

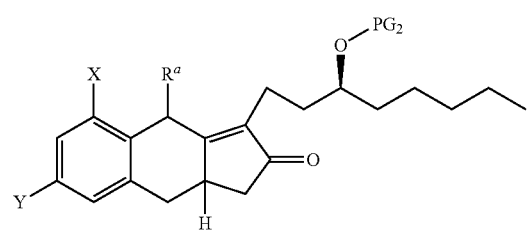
II

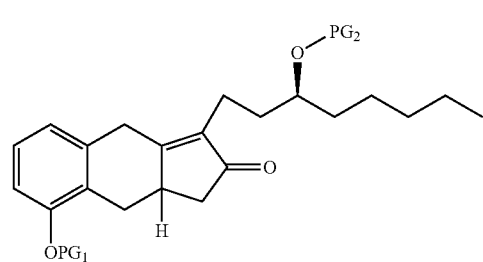
IIb

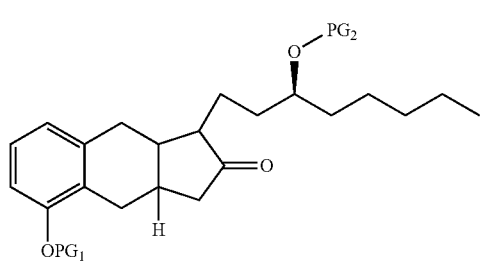
IIIb

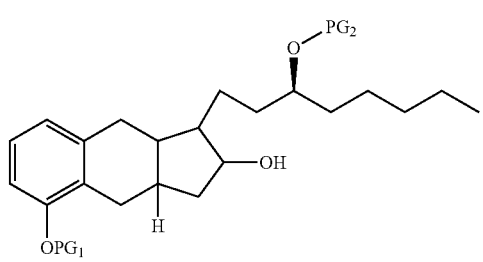
IVb wherein
X and Y are independently of one another selected from the group consisting of H, F, Cl, Br, I, and benzyl; and
$PG_1$ is selected from the group consisting of methyl, methoxymethyl, benzyloxymethyl, methoxyethoxymethyl, benzyl, 4-methoxybenzyl, 2,6-dichlorobenzyl, 3,4-dichlorobenzyl; —CH$_2$COOH, —CH$_2$COOR$_x$, and —CH$_2$CH$_2$OPG$_2$; and
$PG_2$ is THP, SiR$_1$R$_2$R$_3$; or —CH$_2$OR$_x$; and
$R_1$, $R_2$, and $R_3$ are independently from one another selected from the group consisting of methyl, isopropyl, t-butyl, and phenyl $R^a$ is hydrogen, hydroxy —OR$_x$, —OCOOR$_x$, —OSO$_2$R$_x$, Cl, Br F, I, —SR$_x$, or —SO$_2$R$_x$;
$R_x$ is C$_{1-4}$alkyl or aryl; and
wherein at least one of X or Y is not H.

A further embodiment of the invention relates to compounds of formula I, formula II, formula IIb, formula IIIb, or formula IVb as described above, wherein X and Y are independently of one another selected from H, Br or Cl; and at least one of X or Y is not H.

A further embodiment of the invention relates to compounds of formula I, formula II, formula IIb, formula IIIb, or formula IVb as described above, wherein X is Br or Cl; and Y is H, preferably X is Br.

A further embodiment of the invention relates to compounds of formula I, formula II, formula IIb, formula IIIb, or formula IVb as described above, wherein PG$_2$ is THP or TBDMS, preferably PG$_2$ is TBDMS.

Another embodiment of the current invention relates to intermediate compounds of formula I, formula II, formula IIb, formula IIIb, or formula IVb

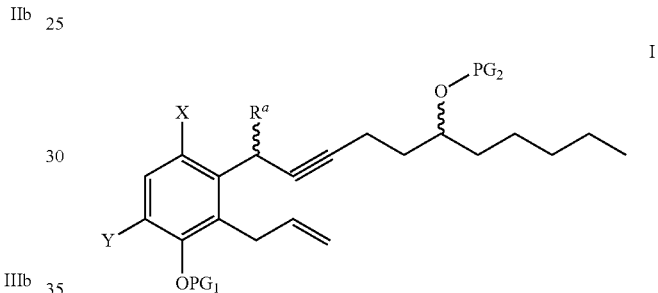
I

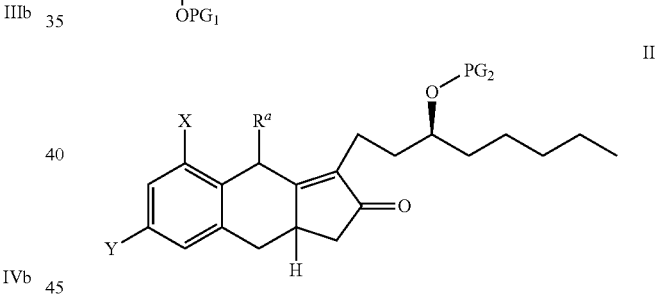
II

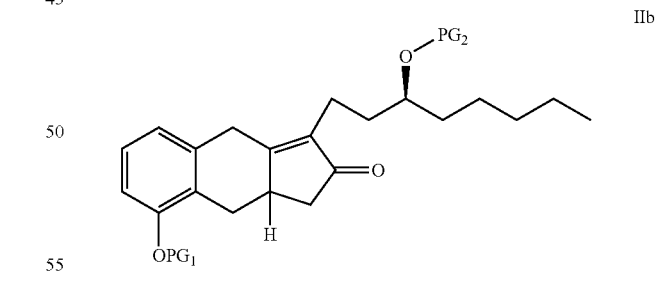
IIb

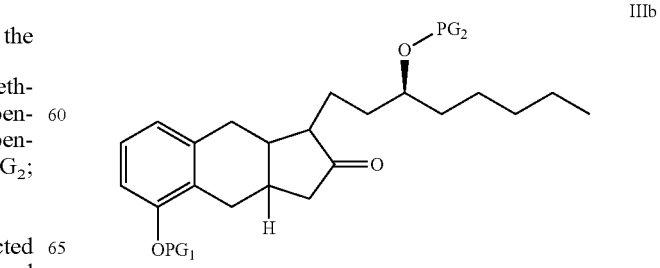
IIIb

-continued

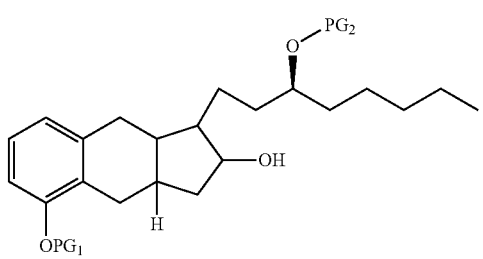

IVb wherein
X and Y are independently of one another selected from the group consisting of H, F, Cl, Br, I, and benzyl; and
$PG_1$ is selected from the group consisting of methyl, methoxymethyl, benzyloxymethyl, methoxyethoxymethyl, benzyl, 4-methoxybenzyl, 2,6-dichlorobenzyl, 3,4-dichlorobenzyl; —$CH_2COOH$, —$CH_2COOR_x$, and —$CH_2CH_2OPG_2$; and $PG_2$ is TBMDS, and
$R^a$ is hydrogen, hydroxy —$OR_x$, —$OCOOR_x$, —$OSO_2R_x$, Cl, Br F, I, —$SR_x$, or —$SO_2R_x$;
$R_x$ is $C_{1-4}$alkyl or aryl; and
wherein at least one of X or Y is not H.

A further embodiment of the invention relates to compounds of formula I or formula II,

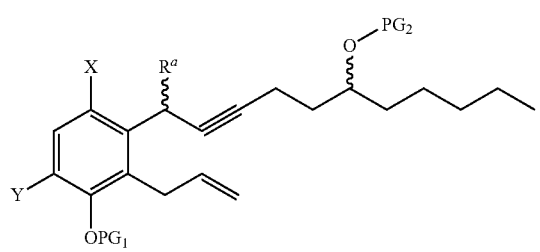

I

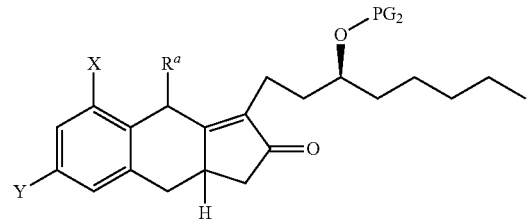

II wherein
X and Y are independently of one another selected from the group consisting of H, F, Cl, Br, I, and benzyl; and
$PG_1$ is selected from the group consisting of methyl, methoxymethyl, benzyloxymethyl, methoxyethoxymethyl, benzyl, 4-methoxybenzyl, 2,6-dichlorobenzyl, 3,4-dichlorobenzyl; —$CH_2COOH$, —$CH_2COOR_x$, and —$CH_2CH_2OPG_2$; and
$PG_2$ is THP, $SiR_1R_2R_3$; or —$CH_2OR_x$; and
$R_1$, $R_2$, and $R_3$ are independently from one another selected from the group consisting of methyl, isopropyl, t-butyl, and phenyl
$R^a$ is hydrogen, hydroxy —$OR_x$, —$OCOOR_x$, —$OSO_2R_x$, Cl, Br F, I, —$SR_x$, or —$SO_2R_x$;
$R_x$ is $C_{1-4}$alkyl or aryl; and
wherein at least one of X or Y is not H.

A further embodiment of the invention relates to a process for making a compound of formula (II), comprising the following step:

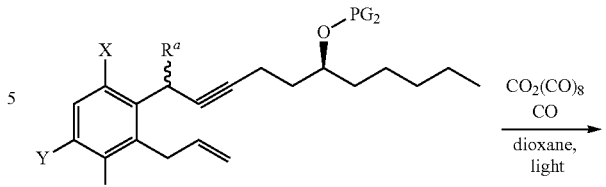

I

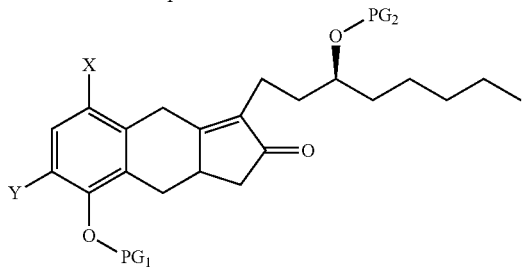

II wherein
X, Y, $R^a$, $PG_1$ and $PG_2$ are as defined above.

A further embodiment of the invention relates to the process as described above, wherein $PG_2$ is TBDMS.

A further embodiment of the invention relates to the process as described above, wherein $R^a$ is hydroxy.

A further embodiment of the invention relates to the process as described above, wherein X is Br, Y is hydrogen, $PG_1$ is benzyl, $PG_2$ is TBDMS; and $R^a$ is hydroxy.

A further embodiment of the invention relates to a process for making a compound of formula IV, comprising the steps of
a) hydrogenating and reducing a compound of formula II to obtain racemic compound of formula III;
b) contacting racemic compound of formula III with Lipase AK in the presence of a solvent; and
c) obtaining an optically pure compound IV;

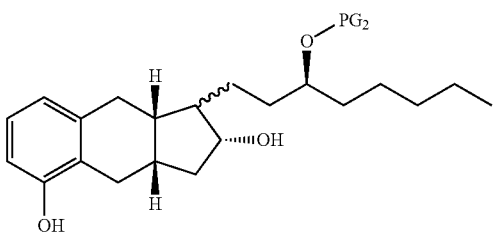

III

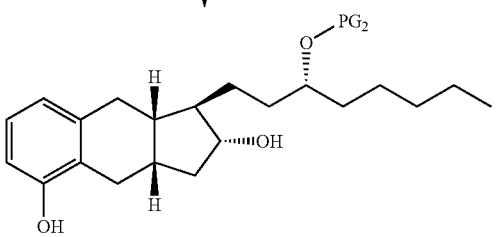

IV wherein
$PG_2$ is THP or TBDMS, preferably $PG_2$ is TBDMS.

A further embodiment of the invention relates to the process as described above, wherein the solvent is selected from the group consisting of vinyl acetate, hexane(s), heptane(s), and chloroform.

A further embodiment of the invention relates to the process according as described above, wherein the hydrogenation is performed at a pH of about 8 to 12, preferabl at pH about 9 to 10.

The subject matter of the following definitions is considered as embodiments of the present invention:

1. A compound of formula I, formula II, formula IIb, formula IIIb, or formula IVb

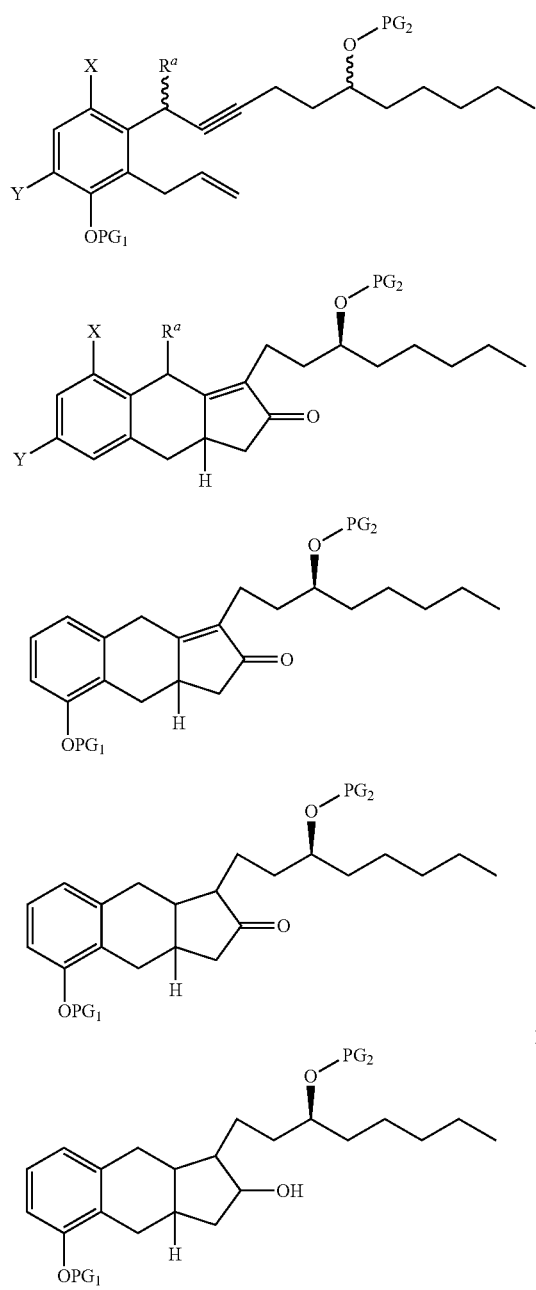

wherein
X and Y are independently of one another selected from the group consisting of H, F, Cl, Br, I, and benzyl; and
$PG_1$ is selected from the group consisting of methyl, methoxymethyl, benzyloxymethyl, methoxyethoxymethyl, benzyl, 4-methoxybenzyl, 2,6-dichlorobenzyl, 3,4-dichlorobenzyl; —CH$_2$COOH, —CH$_2$COOR$_x$, and —CH$_2$CH$_2$OPG$_2$; and $PG_2$ is TBDMS; and
$R^a$ is hydrogen, hydroxy —OR$_x$, —OCOOR$_x$, —OSO$_2$R$_x$, Cl, Br F, I, —SR$_x$, or —SO$_2$R$_x$;
$R_x$ is $C_{1-4}$alkyl or aryl; and
wherein at least one of X or Y is not H.

2. A compound according to claim 1, wherein
X and Y are independently of one another selected from H, Br or Cl; and at least one of X or Y is not H.

3. A compound according to claim 2, wherein
X is Br or Cl; and
Y is H.

4. A compound according to any one of claims 1-3, wherein
X is Br.

5. A compound of formula I, or formula II,

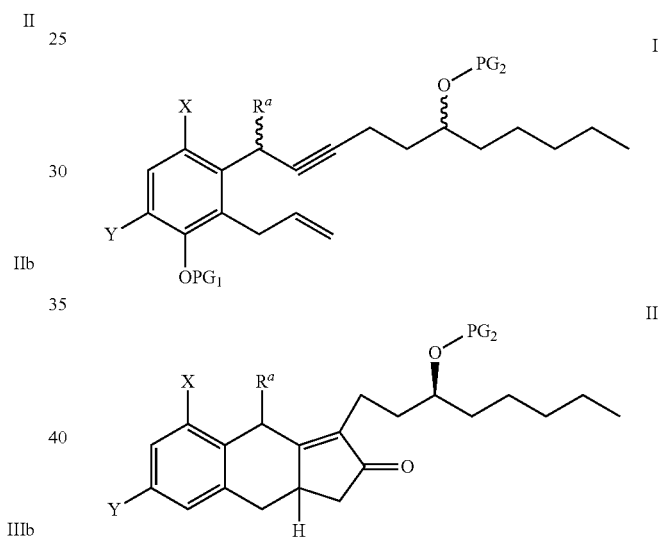

wherein
X and Y are independently of one another selected from the group consisting of H, F, Cl, Br, I, and benzyl; and
$PG_1$ is selected from the group consisting of methyl, methoxymethyl, benzyloxymethyl, methoxyethoxymethyl, benzyl, 4-methoxybenzyl, 2,6-dichlorobenzyl, 3,4-dichlorobenzyl; —CH$_2$COOH, —CH$_2$COOR$_x$, and —CH$_2$CH$_2$OPG$_2$; and
$PG_2$ is THP, SiR$_1$R$_2$R$_3$; or —CH$_2$OR$_x$; and
$R_1$, $R_2$, and $R_3$ are independently from one another selected from the group consisting of methyl, isopropyl, t-butyl, and phenyl
$R^a$ is hydrogen, hydroxy —OR$_x$, —OCOOR$_x$, —OSO$_2$R$_x$, Cl, Br F, I, —SR$_x$, or —SO$_2$R$_x$;
$R_x$ is $C_{1-4}$alkyl or aryl; and
wherein at least one of X or Y is not H.

6. A process for making a compound of formula (II), comprising the following step:

19

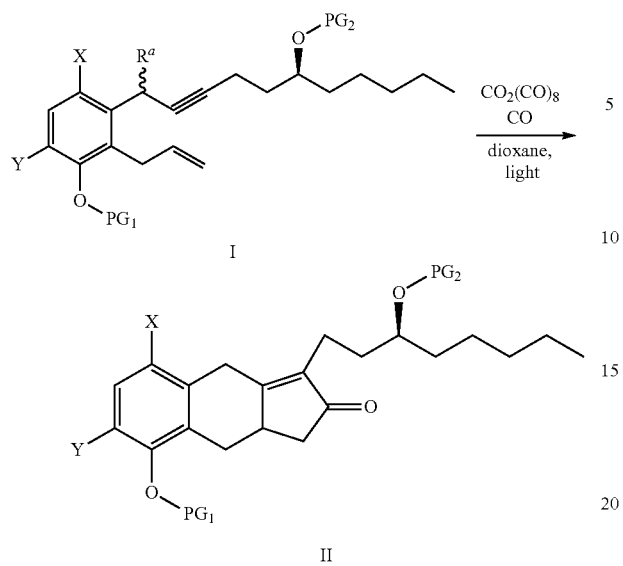

wherein
X, Y, R$^a$, PG$_1$ and PG$_2$ are as defined in claim 1.

7. The process according to claim 6, wherein PG$_2$ is TBDMS.

8. The process according to claim 6 or 7, wherein R$^a$ is hydroxy.

9. The process according to claim 6, wherein
X is Br, and
Y is hydrogen, and
PG$_1$ is benzyl, and
PG$_2$ is TBDMS; and
R$^a$ is hydroxy.

10. A process for making a compound of formula IV, comprising the steps of
a) hydrogenating and reducing a compound of formula II to obtain racemic compound of formula III;

20 b) contacting racemic compound of formula III with Lipase AK in the presence of a solvent; and c) obtaining an optically pure compound IV;

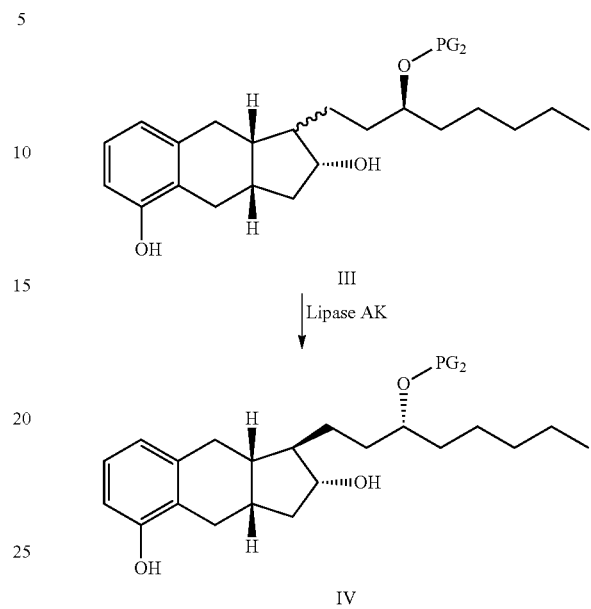

wherein
PG$_2$ is THP or TBDMS.

11. The process according to claim 10, wherein the solvent is selected from the group consisting of vinyl acetate, hexane(s), heptane(s), and chloroform.

12. The process according to claim 10 or 11, wherein the hydrogenation is performed at a pH of about 8 to 12, preferable at pH about 9 to 10.

13. A process for making treprostinil (18) comprising the following steps:

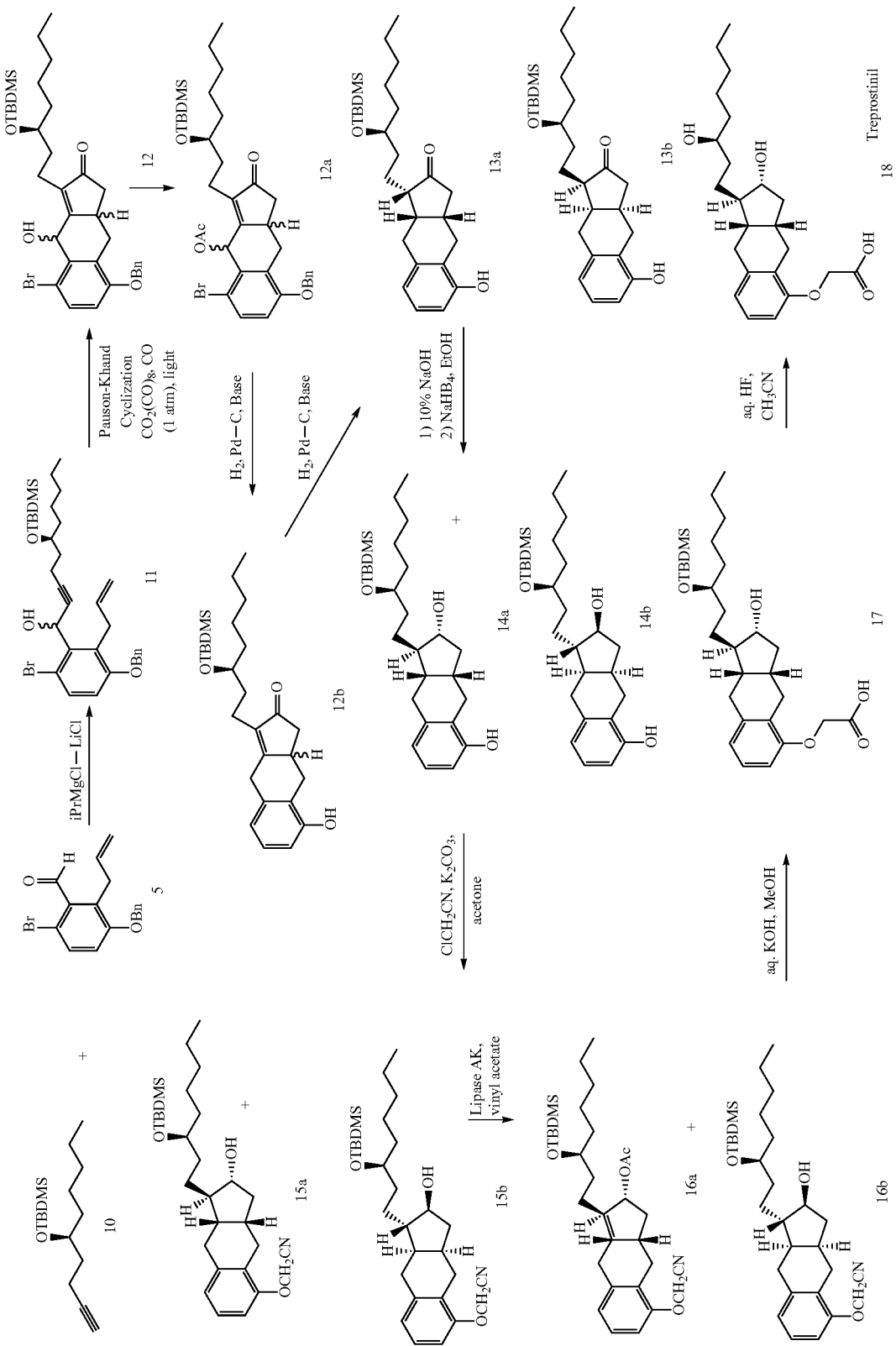

14. A new intermediate compound selected from the group consisting of
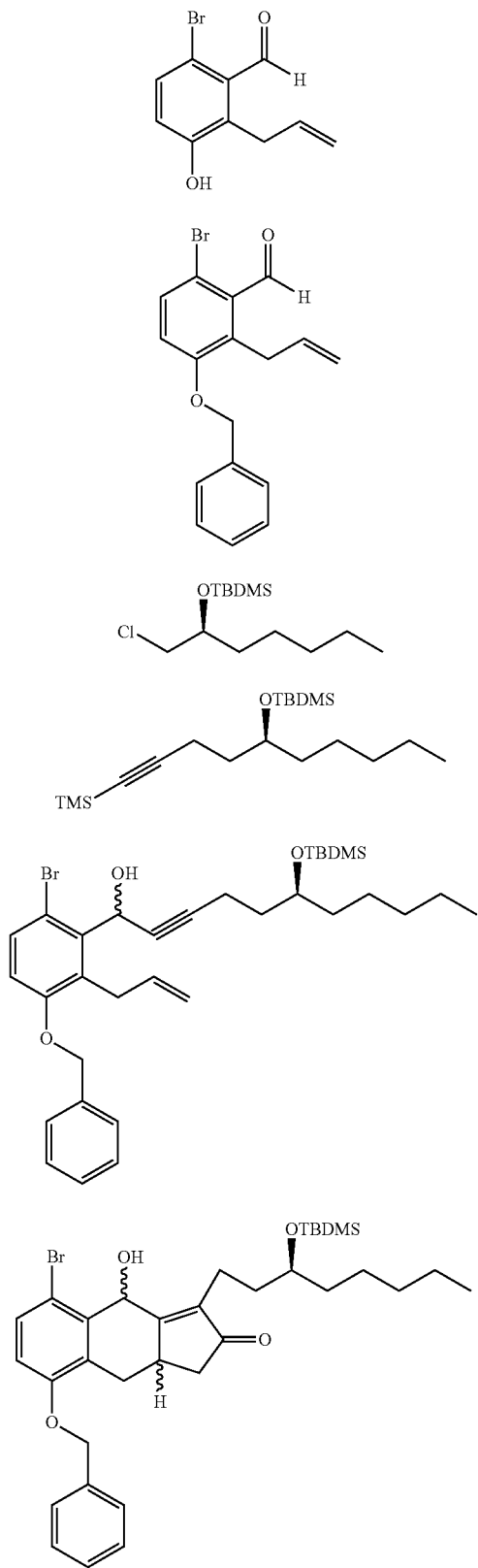
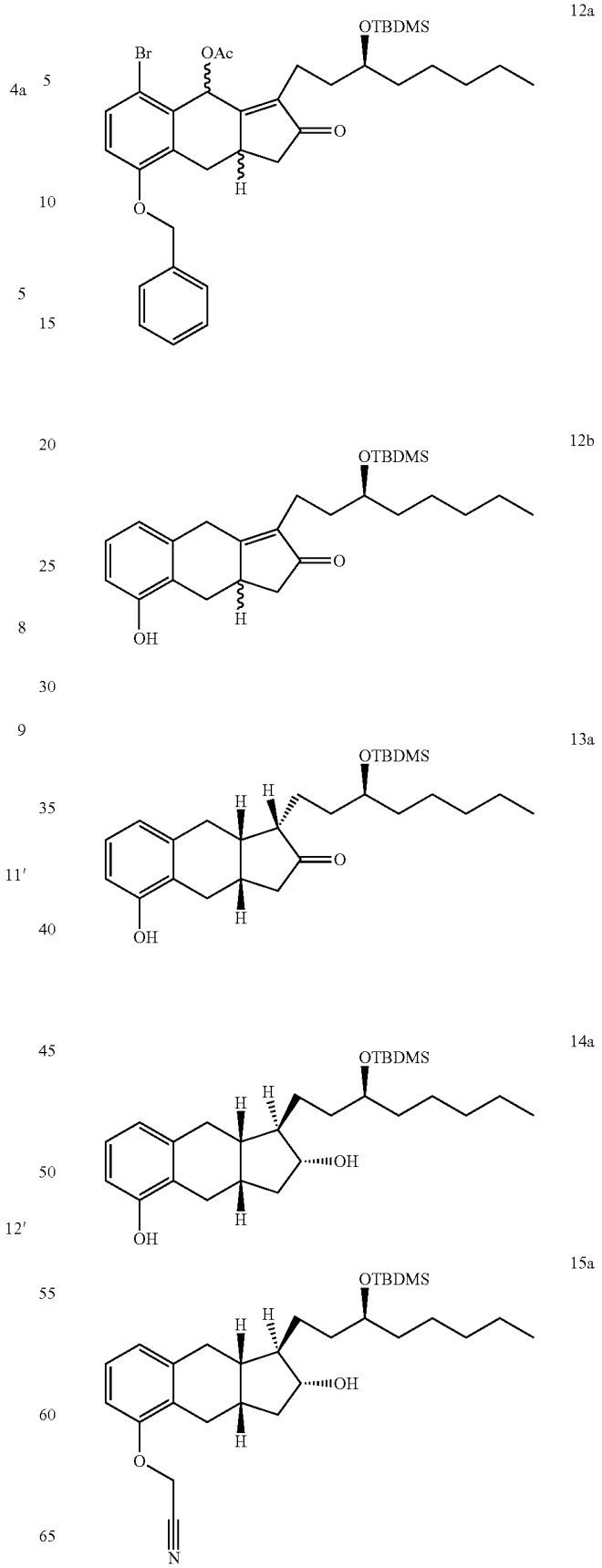

-continued

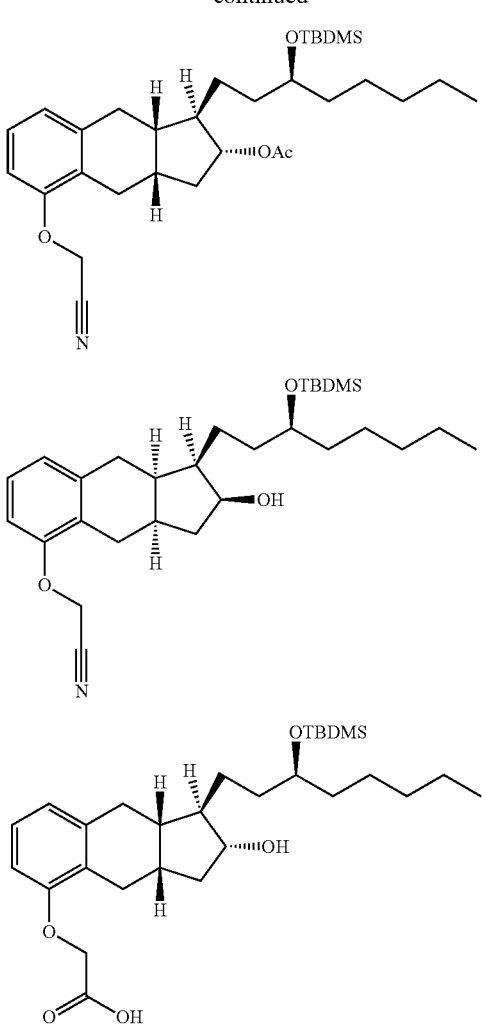

The present invention is further illustrated by, though in no way limited to, the following examples.

EXAMPLES

Preparation of (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid (treprostinil, 18)

Example 1

Preparation of Bromobenzaldehyde 2

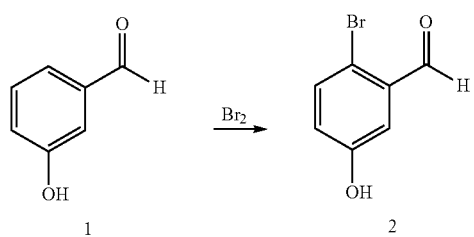

Compound 2 is prepared as described in Bioorganic & Medicinal Chemistry Letters, 20(3), 1169-1172; 2010 or according to Journal of Organic Chemistry, 67(26), 9248-9256; 2002.

Example 2

Preparation of Allylether 3

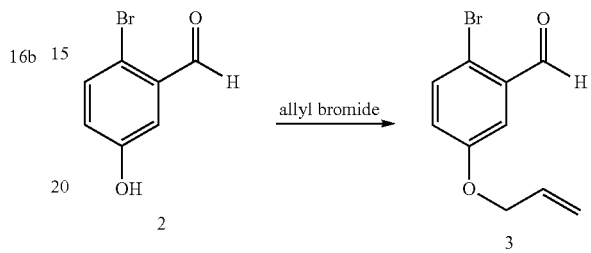

To a dry 5 L three necked round bottom flask fitted with a condensor, temperature port, and stirrer, was added 6-bromo-meta hydroxyl benzaldehyde (2, 250 g, 1.23 moles) in dimethyl formamide (1250 mL). To the resulting solution was added anhydrous pottasium carbonate (538 g, 3.81 moles) under stirring. To this mixture was added slowly allyl bromide and reaction mixture maintained under stirring until the reaction was complete (monitored by thin layer chromatography (TLC) in hexane:dichlor-methane:ethyl acetate::7:4:0.5). After reaction completion dichloromethane and water were added and resulting solution stirred and layer separation carried out. The organic layer treated with 10% NaOH solution and layer separation repeated. The organic layer obtained was distilled out under reduced pressure to obtain 6-bromo-3-allyloxy benzaldehyde as a brownish liquid mass; yield 290 g (98%), purity by HPLC>95%. 1HNMR (CDCl3): 4.55-4.65 (s, 2H), 5.15-5.40 (m, 2H), 6.00-6.10 (m, 1H), 7.0-7.10 (dd, 1H), 7.18-7.24 (d, 1H), 7.52-7.56 (d, 1H), 10.1 (s, 1H, CHO)

Example 3

Claisen Rearrangement to Allyl-Benzaldehydes 4a and 4b (WO0176693)

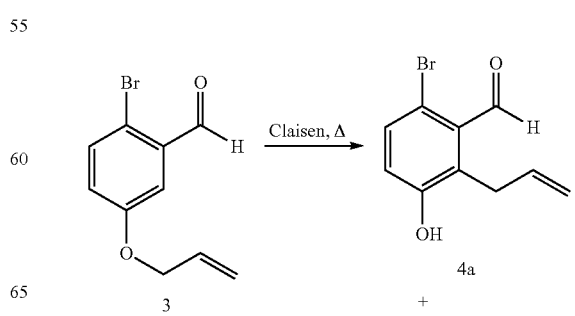

-continued

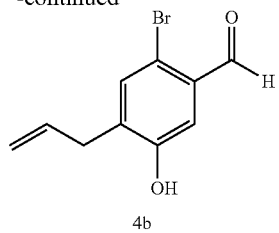

4b

To a 50 L glass flask assemby was added allyl ether (3, 600 g, 2.48 moles) in o-dichlorobenzne (18 L). The resulting solution was heated slowly up to 155° C. in an oil bath and left at temperature for 40 h. The reaction mass was cooled and extracted with 10% NaOH solution. The organic layer of o-dichlorobenzene was taken back into the glass flask assembly and the heating operation was repeated twice. The aqueous layer was treated with HCl and extracted into dichloromethane. The dichoromethane layer was part distilled and hexane added to the flask. This solution was left to stand over a period of 1-2 days under cooling and then filtered using a Bucchner funnel, and the cake was washed with chilled hexane to give 6-bromo-3-hydroxy-2-allyl benzaldehyde as dark brown to blackish colored powder; total yield 160 g (27%), purity by HPLC>93%.

Example 4

Preparation of Benzyl Ether 5

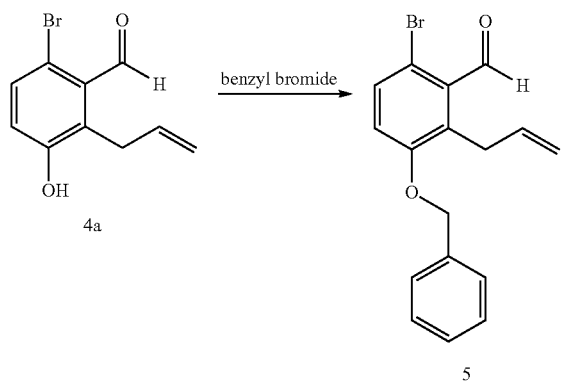 [SMILES: C=CCc1c(O)ccc(Br)c1C=O ; C=CCc1c(OCc2ccccc2)ccc(Br)c1C=O]

To a dry 5 L four necked round bottom flask fitted with a reflux condensor, temperature port, and stirrer was added m-hydroxyl benzaldehyde (4a, 100 g, 0.41 moles) in methanol. To the resulting solution benzyl chloride (175 mL, 1.26 moles) was added. This mixture was then slowly heated to reflux and maintained under stirring for 3-4 h, until the reaction was complete (monitored by TLC in hexane:dichloromethane:ethyl acetate::7:4:0.5). After completion, water and dichloromethane were added. After extraction of the compound into the organic layer and after washing it with 10% NaOH solution, the dichloromethane was distilled off under reduced pressure. Hexane was added to the oily mass and the temperature set to 0-10° C. After stirring for 203 h, the resulting slurry is flitered in a Bucchner funnel and the cake was washed with hexane. to give 6-bromo-3-benzyloxy-2-allyl benzaldehyde as white to off white powder; yield 110 g (80%); purity by HPLC>99%.

Example 5

Preparation of Chloroalcohol 7

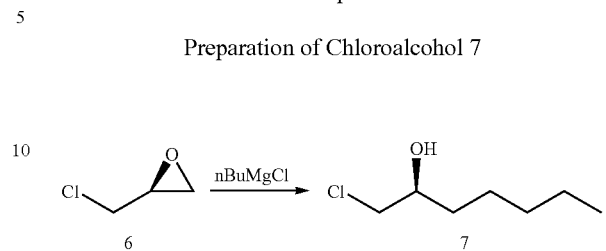

Example 6

Preparation of Tert-Butyldimethylsilyl Ether 8

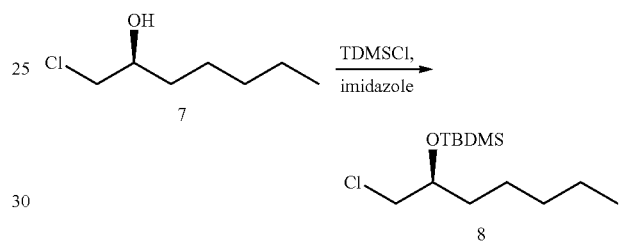

Example 7

Preparation of Trimethylsilylalkyne 9

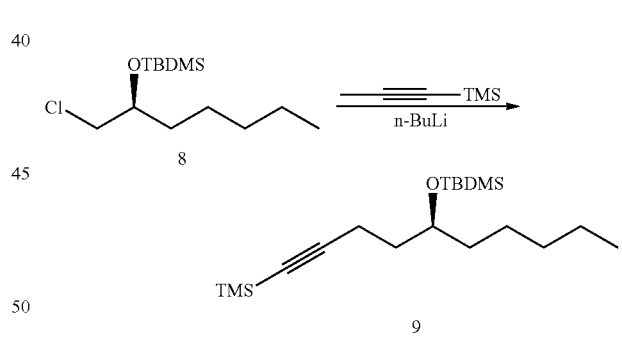

Example 8

Preparation of Alkyne 10

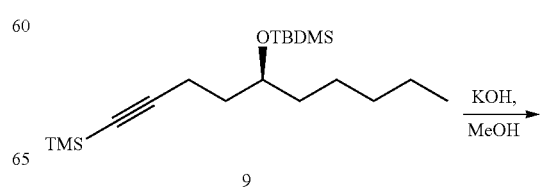

-continued

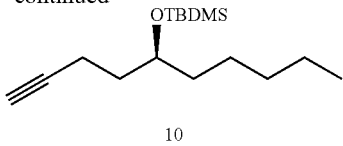

10

Example 9

Preparation of Alkynyl Alcohol 11

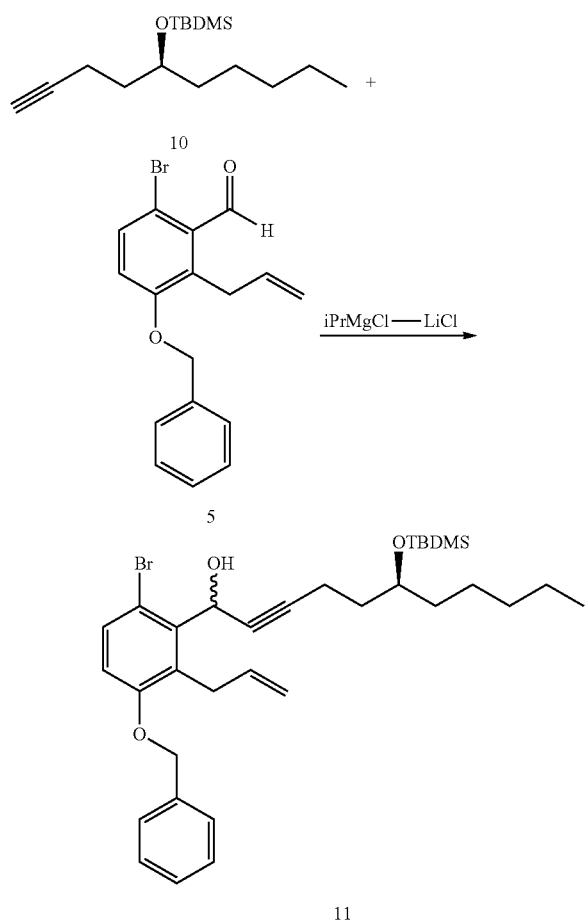

To a solution of 10 (20.3 g; 75.6 mmol) dissolved in 90 mL of dry THF under nitrogen was added isopropylmagnesium chloride lithium chloride complex, 1.3 M in THF (58.1 mL, 75.6 mmol) drop-wise via addition funnel over 10 min. The brown solution was stirred at room temperature (RT) for 15 min. To this solution was added a solution of 5 (12.5 g; 37.8 mmol) in 120 mL of dry THF. The resulting solution was stirred for 1 h at RT. TLC (10% ethyl acetate:hexane-UV detection) indicated the starting material was consumed. The reaction solution was quenched with aqueous ammonium chloride (200 mL) and diluted with 500 mL of tert-butyl methyl ether (MTBE). The layers were separated. The aqueous layer was extracted with MTBE (2×500 mL). The organic layers were combined and dried over anhydrous sodium sulfate. The solvent was filtered through a sintered glass funnel. The filtrate was concentrated in vacuo to give 24.1 g of crude product as oil. The crude product was purified on 330 g Agela silica gel column using an Isco automated chromatography system eluting with 0 to 10% ethyl acetate:hexane to recover 16 g (71%) of 11 as desired product along with 3.7 g (18%) of recovered 10. (NMR, MS)

Example 10

Intramolecular Non-Stereoselective Pauson-Khand Cyclization (PKC) to Cyclopentenone 12

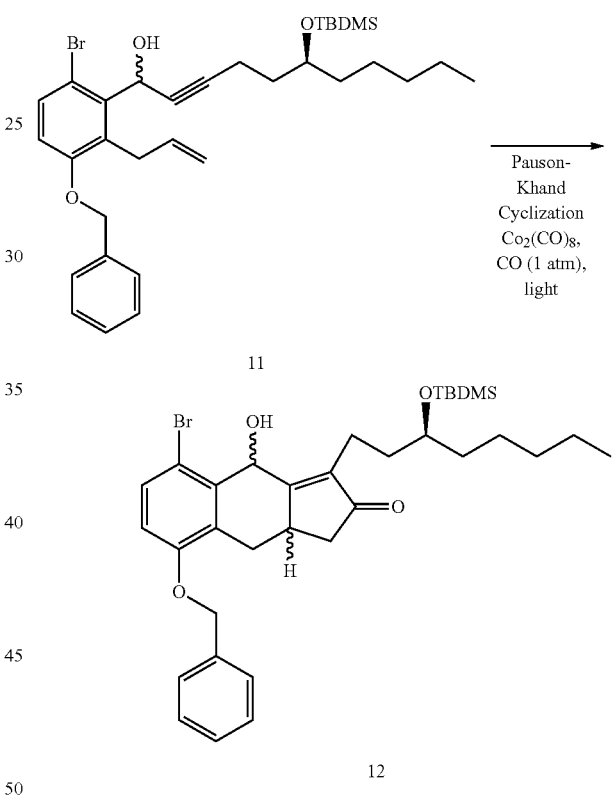

In a 1 L round bottomed flask with magnetic stir bar, reflux condenser, 3 way stopcock vacuum inlet joint and external temperature control, 11 (16.0 g; 26.7 mmol) was dissolved in 271 mL of dioxane at RT. The system was placed under vacuum for 10 seconds followed by a blanket of carbon monoxide. This procedure was repeated twice more. Cobalt carbonyl (3.6 g, 10.5 mmol) was added while the system was under a blanket of carbon monoxide. The system again was evacuated and filled with carbon monoxide. The mixture was stirred while a white light source (300 W bulb) was aimed at the reaction flask maintaining a reaction temperature of 35-40° C. After 48 h, TLC (10% ethyl acetate:hexane UV detection) indicated the starting material was consumed. The filtrate was concentrated in vacuo to afford 18.1 g of crude product as oil. The crude product was purified on silica using SiliaFlash G 60 silica eluting with 5-60% ethyl acetate:hexane to recover 9.2 g (55%) of 12 as desired product. (NMR, MS)

Example 11

Simultaneous Reductive Cleavage of Bromo, Hydroxyl, and Benzyl Ether Moieties and Reduction to Cyclopentanone 13

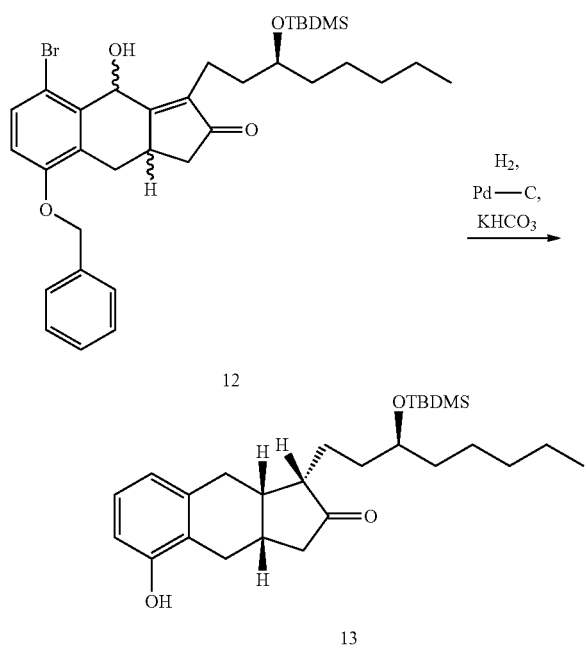

Procedure A

In a 2 L round bottomed flask with magnetic stirrer, 12 (10.0 g; 15.9 mmol) was dissolved in 802 mL of methanol with stirring under nitrogen. Potassium bicarbonate (4.7 g; 47.8 mmol, 3.0 eq.) was added under nitrogen. Nitrogen was bubbled through the solution for 30 min to degass the mixture. At this time, 10% Pd on carbon (4.5 g) was added under nitrogen. Degassing was continued for another 15 min. The reaction mixture was then saturated with hydrogen gas for 20 min. The reaction system was then placed under a hydrogen atmosphere using 6 balloons con-taining hydrogen. The reaction was stirred overnight. TLC (30% ethyl acetate:hexane, UV and ammonium cerium(IV)molybdate stain) indicated that starting material remained. The balloons were recharged with hydrogen gas and the reaction mixture was stirred for another day. After a total of 48 h, TLC indicated no starting material remained. Potassium bicarbonate (3.1 g, 2.0 eq.) was added to the reaction mixture and stirred for 10 min (pH=10). While passing nitrogen gas over the funnel, the reaction mixture was filtered through Whatman quality filter paper, followed by another filtration through a short Celite plug to remove any residual catalyst. The plug was then rinsed with 150 mL of ethyl acetate. The filtrate was concentrated in vacuo to give 14.0 g of a residue. The residue was taken up in 200 mL of ethyl acetate and filtered through Celite again. The Celite plug was rinsed with 150 mL of ethyl acetate. The filtrate was concentrated in vacuo to give 7.1 g of a viscous oil as crude product. The crude product was dissolved in 10 mL of hexane and loaded onto a 120 g Agela silica gel column using an Isco automated chromatography system eluting with 0 to 30% ethyl acetate:hexane to recover 4.0 g (57%) of 13 as desired product (NMR, MS).

Procedure B

In a 3 L round bottom flask (3 neck) with magnetic stirrer, 12 (21.5 g; 34.2 mmol) was dissolved in 1.7 L of methanol with stirring under nitrogen. Potassium bicarbonate (10.2 g; 102.7 mmol, 3.0 eq.) was added under nitrogen. Nitrogen gas was bubbled through the reaction mixture for 30 min to degas. After 30 min of degassing, 10% Pd on carbon (9.6 g) was added under nitrogen. Degassing was continued for another 15 min. At this time, hydrogen gas was bubbled into the reaction mixture for 20 min. 6 balloons were attached to the reaction flask and the system was stirred under an atmosphere of hydrogen overnight. TLC (30% ethyl acetate:hexane, UV detection and ammonium cerium(IV)molybdate stain) indicated that starting material remained. The balloons were recharged with hydrogen gas and the reaction mixture was stirred for another day. After 48 h, TLC indicated some starting material remained. The balloons were recharged and the reaction mixture was stirred for another day. After 72 h, TLC indicated no starting material remained. Potassium bicarbonate (6.8 g; 67.9 mmol, 2 eq.) was added to the reaction mixture and the reaction mixture was stirred for 10 min. While under a blanket of nitrogen, the reaction mixture was filtered through Whatman filter paper, followed by a Celite plug to remove any residual catalyst. The filtrate was used as is in the next step.

Example 12

Stereoselective Sodium Borohydride Reduction to Cyclopentanol (14)

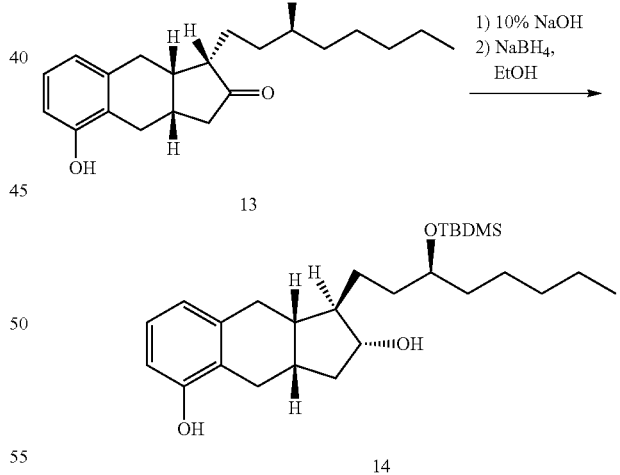

Procedure a (Uses Purified Compound from the Hydrogenation Reaction):

A portion of 13 (3.0 g; 6.7 mmol) in 260 mL of methanol was treated with 1.4 mL of 10% NaOH at RT and stirred under nitrogen. After 90 min, TLC, (20% ethyl acetate:hexane, UV detection and ammonium cerium(IV)molybdate stain) indicated the bottom spot disappeared. The reaction solution was cooled to −10° C. and sodium borohydride was added (255 mg; 6.7 mmol). After 1 h, TLC (30% ethyl acetate:hexane) indicated starting material remained. Another 255 mg (6.7 mmol) of sodium borohydride was added. After 2 h at −10° C., TLC indicated no starting materials remained. The reaction was allowed to warm to RT and stirred overnight. The reaction mixture was acidified to pH 6 with acetic acid. The reaction was diluted with 100 mL of water and concentrated in vacuo. The residue was diluted with ethyl acetate (300 mL), washed with 25 mL of 5% sodium bicarbonate (1×100 mL) and brine (1×100 mL). The organic layer was dried over anhydrous sodium sulfate and filtered through a sintered glass funnel. The filtrate was concentrated in vacuo to recover 3.0 g of crude product. The crude product was dissolved in 15 mL of hexane and loaded onto a 40 g Agela silica column. The column was placed on an automated Isco chromatography system. The crude product was eluted from 0 to 15% ethyl acetate:hexane over 20 min, 15-20% ethyl acetate:hexane over 5 min, 20-25% ethyl acetate:hexane over 5 min and finally 25-40% ethyl acetate to recover 1.7 grams (57%) of 14 as desired product.

Procedure B (Uses the Reaction Filtrate from the Hydrogenation):

In a 5 L round bottom flask, 3000 mL (73.5 mmol) of 13 reaction filtrate was treated with 160 mL of 10% NaOH at RT and stirred under nitrogen. After 2 h, TLC (20% ethyl acetate:hexane, UV detection and ammonium cerium(IV)molybdate stain) indicated the bottom epimer (spot) disappeared. The reaction solution was cooled to −10° C. Sodium borohydride (3.1 g; 84.2 mmol) was added in one portion. After 1 h, TLC (30% ethyl acetate:hexane, UV detection and ammonium cerium(IV)molybdate stain) indicated that starting material remained. Another 3.1 g (84.2 mmol) of sodium borohydride was added. After a total of 2 h at −10° C., TLC indicated no starting material remained. The reaction was allowed to warm to RT and stirred overnight. The reaction mixture was acidified to pH 6 with acetic acid. The reaction was diluted with 200 mL of water and concentrated in vacuo. The residue was diluted with ethyl acetate (1600 mL), washed with 25 mL of 5% sodium bicarbonate(1×500 mL) and brine (1×300 mL). The organic layer was dried over anhydrous sodium sulfate and filtered through a sintered glass funnel. The filtrate was concentrated in vacuo to recover 38.4 g of crude product. The crude product was dissolved in 65 mL of hexane and loaded onto a 770 g SilicaFlash G60 column and eluted with 5% ethyl acetate:hexane (1×1000 mL), 10% ethyl acetate:hexane (1×1000 mL), 15% ethyl acetate:hexane (1×1000 mL), 20% ethyl acetate:hexane (1×1000 mL), 25% ethyl acetate:hexane (1×1000 mL), 30% ethyl acetate:hexane (1×1000 mL), 35% ethyl acetate:hexane (1×1000 mL) and 40% ethyl acetate:hexane (1×500 mL) to afford 16.7 grams (44% yield) of desired product 14.

Example 13

Alkylation of Phenol (15)

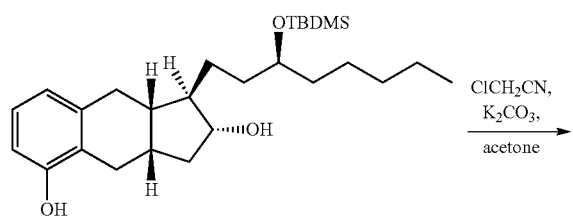

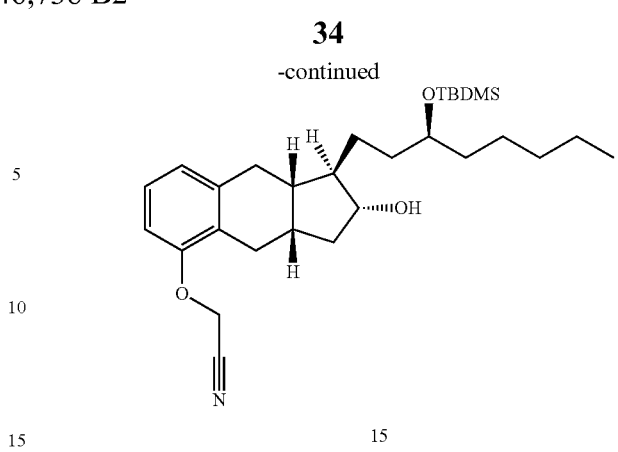

To a solution of 14 (0.5 g; 1.11 mmol) in acetone (45 mL) under argon was added potassium carbonate (1.5 g; 11.1 mmol, 10 eq,) while a stream of argon gas was passed through the mixture for 5 min. Chloroacetonitrile (1.4 mL; 22.3 mmol, 20 eq.) was added and the mixture was heated to reflux for 5 h. TLC (25% ethyl acetate:hexane) indicated the reaction was complete. The reaction mixture was cooled to RT and filtered through a Celite plug. The filtrate was concentrated in vacuo to give 1.8 g of crude product as an oil. The oil was stored at 0° C. overnight. The crude product was dissolved in 10 mL of 20% ethyl acetate:hexane and passed through Siliaflash silica gel eluting with 20% ethyl acetate:hexane (2×100 mL). The solvent was concentrated in vacuo to recover 0.48 g of an oil. The silica plug was then rinsed with 50% ethyl acetate:hexane (3×100 mL), TLC indicated that desired product was present in both fractions. The fractions were combined and purified. The crude product was dissolved in 8 mL of hexane and loaded onto a 12 gram Agela silica column. The crude product was eluted with 0 to 30% ethyl acetate:hexane for 20 min to recover 0.35 g (65%) of 15a as desired product.

Example 14

Enzymatic Resolution with Lipase AK to Diastereomerically Pure Acetate (16a)

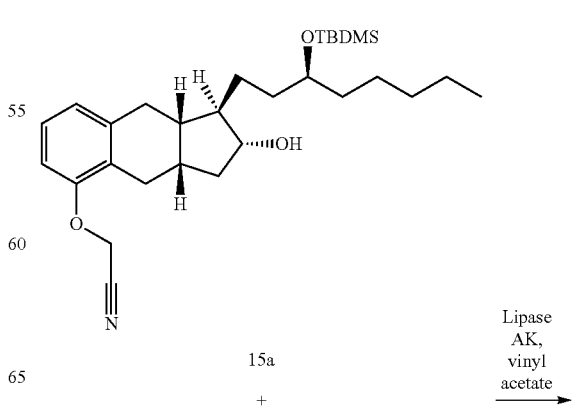

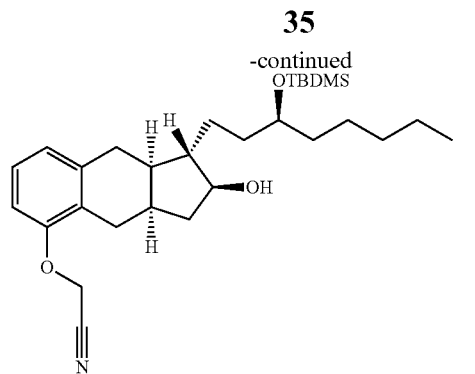

15b

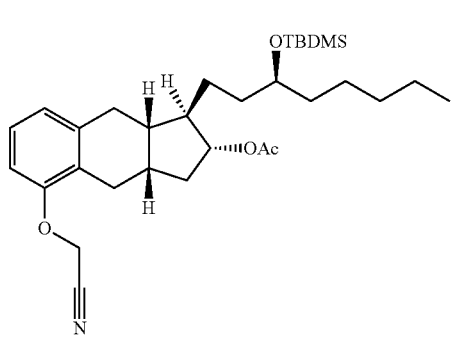

16a

+

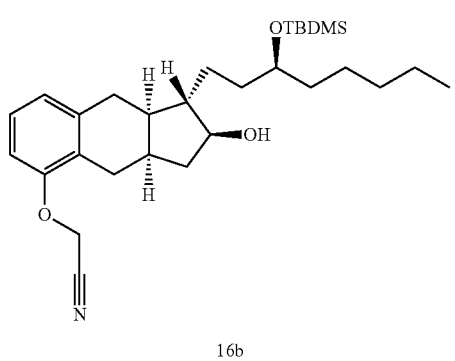

16b

A portion of 15 (18.6 g; 38.2 mmol) was dissolved in 400 mL of dry hexane at RT. Vinyl acetate (50 mL) and Lipase AK "AMANO" (36 g) was added in one portion. The mixture was stirred for 48 h under nitrogen. TLC (20% ethyl acetate: hexane) indicated both spots are present in equal UV intensity. This was confirmed by 1H-NMR. The reaction mixture was filtered through a sintered glass funnel and rinsed with 250 mL of 1:1 hexane:ethyl acetate. The filtrate was concentrated in vacuo to recover about 21 g of an oil. The crude product was dissolved in 50 mL of hexane and loaded onto a 330 g Agela silica column. The column was placed on an automated Isco chromatography system. The crude product was eluted with 10-20% ethyl acetate:hexane for 20 min to recover 8.7 g (43%) of the desired isomer as 16a as well as 8.6 g (43%) of the resolved alcohol 16b.

Example 15

Preparation of Phenoxy-Acetic Acid (17)

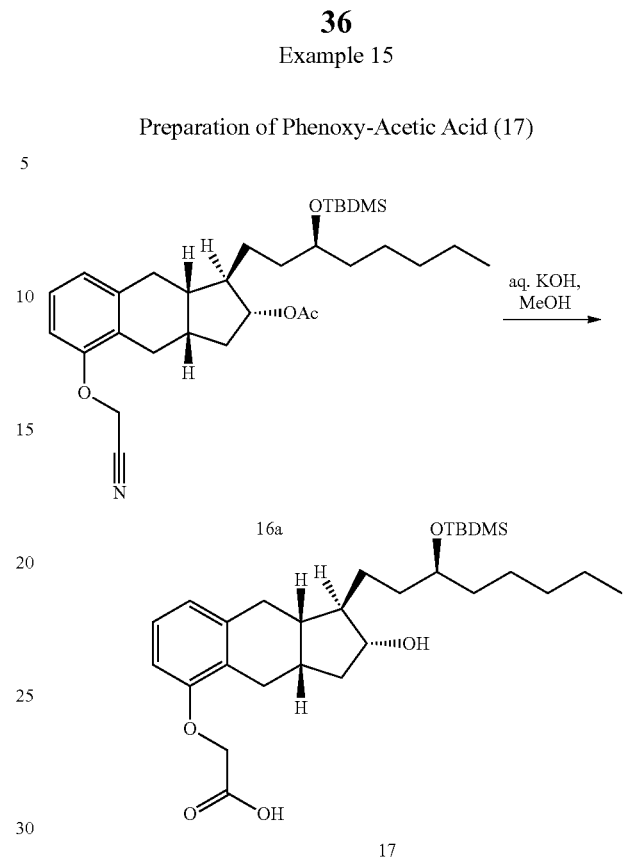

A portion of 16a (15.8 g; 29.9 mmol) was dissolved in 748 mL of MeOH. 35% aq. KOH (262 mL) was added in portions over 5 min. The reaction was heated to reflux. After 1 h TLC (30% ethyl acetate:hexane) indicated no starting material remained. After 4 h, TLC (100% ethyl acetate) indicated a heavy UV active spot above the origin. The reaction mixture was cooled to RT, then placed in an ice bath. 2M HCl (600 mL) was added to acidify the reaction to pH 5. The reaction mixture was diluted with 1.6 L of ethyl acetate and washed with sat. NaCl (1.6 L). The organic layer was dried over anhydrous sodium sulfate. The solvent was filtered through a sintered glass funnel. The filtrate was concentrated in vacua to recover 15.1 g of 17 as viscous oil which was taken onto the next step.

Example 16

Preparation of Treprostinil (18)

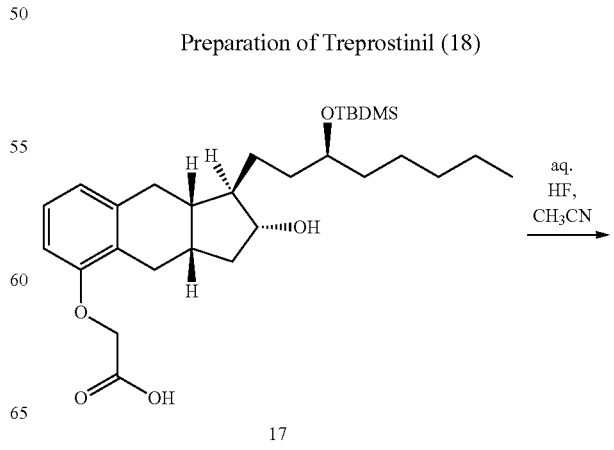

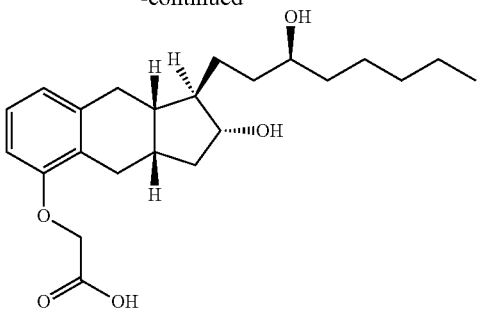

18
Treprostinil

A portion of 17 (15.1 g; 29.9 mmol) was dissolved in 300 mL of acetonitrile. The solution was cooled to 0° C. 73 mL of 48% HF was carefully added in portions. After 5 min, TLC (100% ethyl acetate) indicated no starting material remained. The reaction was stored at −20° C. overnight. The reaction was warmed to RT and with vigorous stirring was diluted with 1.5 L of distilled water. A precipitate was formed and stirring was continued for 5 min. The solid was allowed to settle and filtered through a Buchner funnel. The solid was rinsed with 250 mL of distilled water. The solid was dried under vacuum for 30 min. The solid was placed under high vacuum for 5 h at RT. 17.6 g of solid was recovered. The material was stirred in 300 mL of hexane for 5 h. The solid was filtered through a Buchner funnel and dried under vacuum for 15 min. Finally the material was placed on the lyophilizer for 48 h to remove any trace solvents. 10.5 g (91%) of treprostinil (18) were recovered as desired product.

It will be apparent to those skilled in the art that various modifications and variations can be made to the processes and novel intermediates of this invention. Thus, it is intended that the present invention cover such modifications and variations, provided they come within the scope of the appended claims and their equivalents.

The invention claimed is:

1. A compound of the following formula I or formula II:

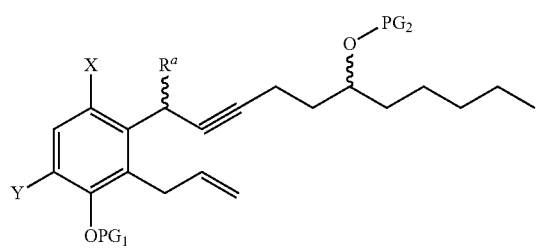

I

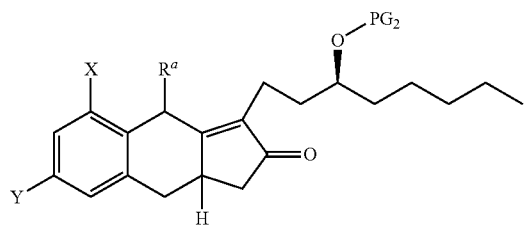

II wherein:

X is Br and Y is H;

PG$_1$ is selected from the group consisting of methyl, methoxymethyl, benzyloxymethyl, methoxyethoxymethyl, benzyl, 4-methoxybenzyl, 2,6-dichlorobenzyl, 3,4-dichlorobenzyl, —CH$_2$COOH, —CH$_2$COOR$_x$, and —CH$_2$CH$_2$OPG$_2$;

PG$_2$ is tert-butyl-dimethylsilyl (TBDMS), tetrahydropyran (THP), SiR1R2R3, or —CH2ORx;

R$^a$ is hydrogen, hydroxy —OR$_x$, —OCOOR$_x$, —OSO$_2$R$_x$, Cl, Br, F, I, —SR$_x$, or —SO$_2$R$_x$; and R$_x$ is C$_{1-4}$alkyl or aryl.

2. The compound of claim 1, wherein PG$_2$ is TBDMS.

3. The compound of claim 1, wherein PG$_2$ is THP.

4. The compound of claim 1, wherein PG$_1$ is benzyl.

5. The compound of claim 1, wherein R$^a$ is hydrogen.

6. The compound of claim 1, wherein R$^a$ is hydroxy.

7. The compound of claim 1, wherein the compound is of formula I:

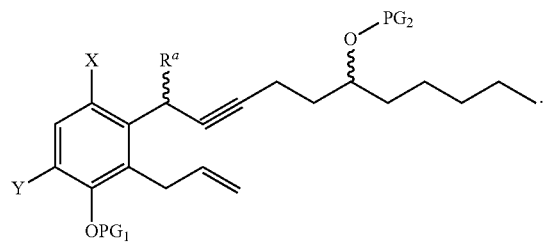

8. The compound of claim 7, wherein PG$_2$ is TBDMS.

9. The compound of claim 7, wherein PG$_2$ is THP.

10. The compound of claim 7, wherein PG$_1$ is benzyl.

11. The compound of claim 7, wherein R$^a$ is hydrogen.

12. The compound of claim 7, wherein R$^a$ is hydroxy.

13. The compound of claim 1, wherein the compound is of formula II:

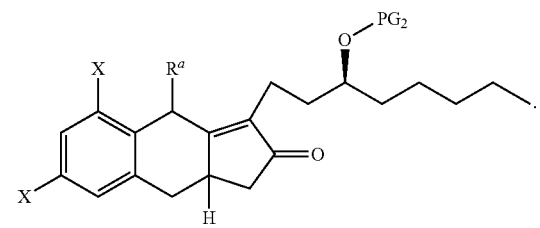

14. The compound of claim 13, wherein PG$_2$ is TBDMS.

15. The compound of claim 13, wherein PG$_2$ is THP.

16. The compound of claim 13, wherein R$^a$ is hydrogen.

17. The compound of claim 13, wherein R$^a$ is hydroxy.

* * * * *